(12) United States Patent
Boomgaarden

(10) Patent No.: US 7,519,441 B2
(45) Date of Patent: Apr. 14, 2009

(54) SYSTEMS, METHODS AND APPARATUS FOR POWERED ASSISTANCE OF A MOTORIZED SUPPORT DEVICE

(75) Inventor: Jonathon Carl Boomgaarden, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 467 days.

(21) Appl. No.: 11/241,076

(22) Filed: Sep. 30, 2005

(65) Prior Publication Data

US 2007/0078534 A1    Apr. 5, 2007

(51) Int. Cl.
*G05B 19/18* (2006.01)
*H05G 1/02* (2006.01)

(52) U.S. Cl. .............. 700/63; 700/56; 700/61; 378/197

(58) Field of Classification Search ............ 700/63, 700/56, 61; 378/167, 189, 195–197
See application file for complete search history.

(56) References Cited

U.S. PATENT DOCUMENTS

| | | | |
|---|---|---|---|
| 3,155,383 A | 11/1964 | Whitmore | |
| 4,021,715 A * | 5/1977 | Von Hacht et al. | 318/628 |
| 4,630,872 A | 12/1986 | Teramachi | |
| 4,671,728 A | 6/1987 | Clark et al. | |
| H313 H | 7/1987 | Staudenmann et al. | |
| 4,769,565 A | 9/1988 | Teramachi | |
| 5,048,069 A | 9/1991 | Sizcek | |
| 5,050,202 A * | 9/1991 | Yanome | 378/195 |
| 5,157,707 A | 10/1992 | Ohlson | |
| 5,388,913 A | 2/1995 | Cawley et al. | |
| 5,506,879 A | 4/1996 | Mori et al. | |
| 5,636,259 A | 6/1997 | Khutoryansky et al. | |
| 5,658,078 A | 8/1997 | Cawley | |
| 5,671,266 A * | 9/1997 | Linhart | 378/195 |
| 5,751,788 A | 5/1998 | Khutoryansky et al. | |
| 5,768,336 A | 6/1998 | Khutoryansky et al. | |
| 5,870,450 A | 2/1999 | Khutoryansky et al. | |
| 5,917,882 A | 6/1999 | Khutoryansky et al. | |
| 6,128,006 A | 10/2000 | Rosenberg et al. | |
| 6,155,716 A | 12/2000 | Okamura et al. | |
| 6,240,582 B1 | 6/2001 | Reinke | |
| 6,282,264 B1 | 8/2001 | Smith et al. | |
| 6,459,226 B1 * | 10/2002 | Zettel et al. | 318/560 |
| 6,552,499 B2 | 4/2003 | Derra et al. | |
| 6,857,147 B2 | 2/2005 | Somasundaram | |
| 6,952,180 B2 | 10/2005 | Jonsson | |
| 6,986,179 B2 | 1/2006 | Varadharajulu | |
| 7,177,393 B2 * | 2/2007 | Kanemitsu | 378/117 |
| 2002/0112016 A1 * | 8/2002 | Peshkin et al. | 709/208 |
| 2003/0095635 A1 | 5/2003 | Moritake et al. | |
| 2004/0131159 A1 | 7/2004 | McKenna | |

* cited by examiner

*Primary Examiner*—Albert DeCady
*Assistant Examiner*—Steven R Garland
(74) *Attorney, Agent, or Firm*—Peter Vogel, Esq.; William Baxter, Esq.; Michael G. Smith, Esq.

(57) ABSTRACT

Systems, methods and apparatus are provided through which movement of a medical imaging device is detected and the movement is assisted in magnitude by an external force.

20 Claims, 13 Drawing Sheets

SYSTEMS, METHODS AND APPARATUS FOR POWERED ASSISTANCE OF A MOTORIZED SUPPORT DEVICE

RELATED APPLICATION

This application is related to copending U.S. application Ser. No. 10/966,504 filed Oct. 15, 2004 entitled "SYSTEMS, METHODS AND APPARATUS OF A RADIOGRAPHIC POSITIONER."

FIELD OF THE INVENTION

This invention relates generally to positioning apparatus, and more particularly to control logic to operate the positioning apparatus.

BACKGROUND OF THE INVENTION

Conventional radiographic examination rooms include a radiographic table and/or radiographic wallstand. The radiographic table and/or radiographic wallstand each contain an image receptor. Medical imaging equipment such as an X-ray source and the collimator is mounted to an overhead tube support (OTS) in the vicinity of the radiographic table and/or the radiographic wallstand for performing diagnostic imaging procedures. The X-ray source and the collimator comprise a tube mount assembly.

The tube mount assembly is aligned with the receptor for imaging of a subject. To align the tube mount assembly with a receptor, the tube mount assembly and OTS move in three linear motions (lateral, longitudinal, vertical) which are perpendicular to each other, and the tube mount assembly moves in two rotational rotations (rotation about the vertical axis, and rotation about one horizontal axis), for a total of five axes.

Manual positioning of the X-ray source, collimator and OTS is performed by an operator releasing locks on each of the five axes, moving the tube mount assembly to a position of alignment with a receptor, the position being indicated by a "detent," and stopping the tube mount assembly at that position for each of the five axes. The detent is a means of indicating to the operator that the OTS has reached an aligned position along. When the operator moves the tube mount assembly, the operator must have the strength and the reach to push the tube mount assembly to a destination position. This movement can be difficult, causing fatigue of the operator.

For the reasons stated above, and for other reasons stated below which will become apparent to those skilled in the art upon reading and understanding the present specification, there is a need in the art to more easily move the tube mount assembly or other positioning apparatus, or medical imaging equipment.

BRIEF DESCRIPTION OF THE INVENTION

The above-mentioned shortcomings, disadvantages and problems are addressed herein, which will be understood by reading and studying the following specification.

In one aspect, the operator pushes a lock release switch or button, which releases an axis of motion so that manual motion may occur. The operator exerts force on the equipment to overcome the resistance to motion. As the equipment begins to move as a result of the operator exerted force, the motion is sensed, and based on the direction of motion, a motor is engaged to apply a force which assists the operator in moving the equipment, which solves the need in the art to more easily move the tube mount assembly.

In a further aspect, a medical imaging positioning apparatus is moved by first determining a direction of a manually-propelled movement of the medical imaging positioning apparatus and then applying a kinetic assistance to the medical imaging positioning apparatus in the direction. The application of the kinetic assistance provides easier movement than the manual movement by the operator.

In another aspect, the determining movement of the medical imaging positioning apparatus includes sampling at least one position sensor over a number times to detect movement of the medical imaging positioning apparatus and/or receiving at least one signal from a movement sensor of the medical imaging positioning apparatus. Examples of the position sensor are an encoder, a potentiometer and a resolver. One example of a movement sensor is a velocity sensor such as a tachometer.

In yet another aspect, a table of forces and positions is used in the determination of the movement of the medical imaging positioning apparatus. In some embodiments, the table of forces and positions is generated by driving the medical imaging positioning apparatus through a range of motion, and recording the forces and positions during the driving.

In still another aspect, applying kinetic assistance to the medical imaging positioning apparatus includes determining if a speed of the medical imaging positioning apparatus is greater than a maximum speed at which the powered assist is allowed to operate, and if so, then removing the kinetic assistance, by decoupling or disengaging the drive from the positioning apparatus.

In yet a further aspect, moving the medical imaging positioning apparatus also includes determining that an operator of the medical imaging positioning apparatus intends to move the medical imaging positioning apparatus and then unlocking movement of the medical imaging positioning apparatus.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into five sections. In the first section, a system level overview is described. In the second section, embodiments of methods are described. In the third section, embodiments of apparatus are described. In the fourth section, the hardware and the operating environment in conjunction with which embodiments may be practiced are described. Finally, in the fifth section, a conclusion of the detailed description is provided.

System Level Overview

Figure 1:
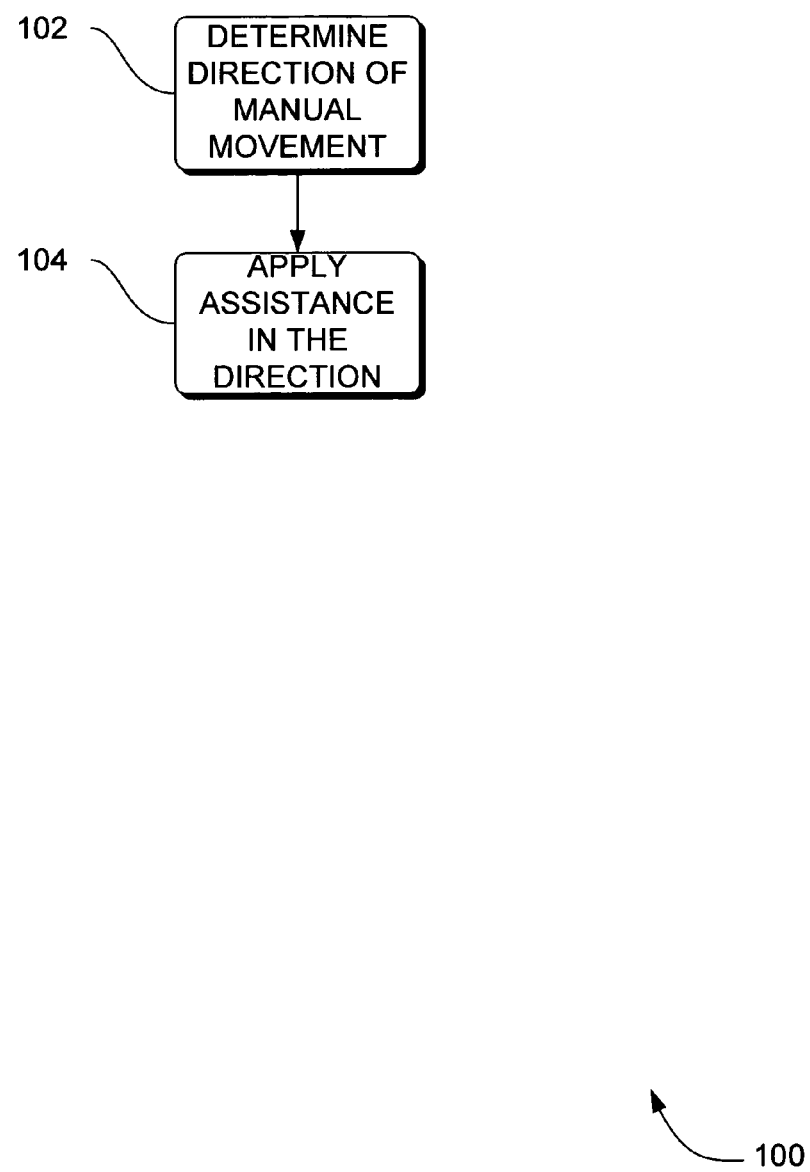
FIG. 1 is a flowchart that provides an overview of a method to provide a kinetic assistance in a movement of a medical imaging positioning apparatus.

FIG. 1 is a flowchart that provides an overview of a method 100 to provide a kinetic assistance in a movement of a medical imaging positioning apparatus. Method 100 solves the need in the art to more easily move the medical imaging positioning apparatus.

Method 100 includes determining 102 one or more directions of manually-propelled movement of the positioning apparatus of the medical imaging equipment or of the medical imaging equipment. The directions of movement can be about either of two rotation axes, or along any one of three axes, longitudinal lateral and vertical; or the movement can be in any combination of three axes and/or rotations. Various embodiments of the determining action 102 are described in FIGS. 2, 3 and 4 below. One example of the medical imaging equipment is a medical X-ray imaging source. Various examples of the positioning apparatus of the medical imaging equipment are described in FIGS. 10, 11 and 12 below such as a tube mount assembly.

Method 100 also includes applying 104 or directing a kinetic assistance to the medical imaging positioning apparatus in the one or more directions. Various embodiments of the determining are described in FIGS. 5 and 6 below. Applying 104 the kinetic assistance solves the need in the art to more easily move the tube mount assembly.

While method 100 is not limited to any particular medical imaging equipment, positioning apparatus, kinetic assistance, application of kinetic assistance or direction of movement, for sake of clarity, simplified medical imaging equipment, positioning apparatus, kinetic assistance, application of kinetic assistance and direction of movement are described.

Methods of an Embodiment

In the previous section, apparatus of the operation of an embodiment was described. In this section, the particular methods of such an embodiment are described by reference to a series of flowcharts.

Figure 2:
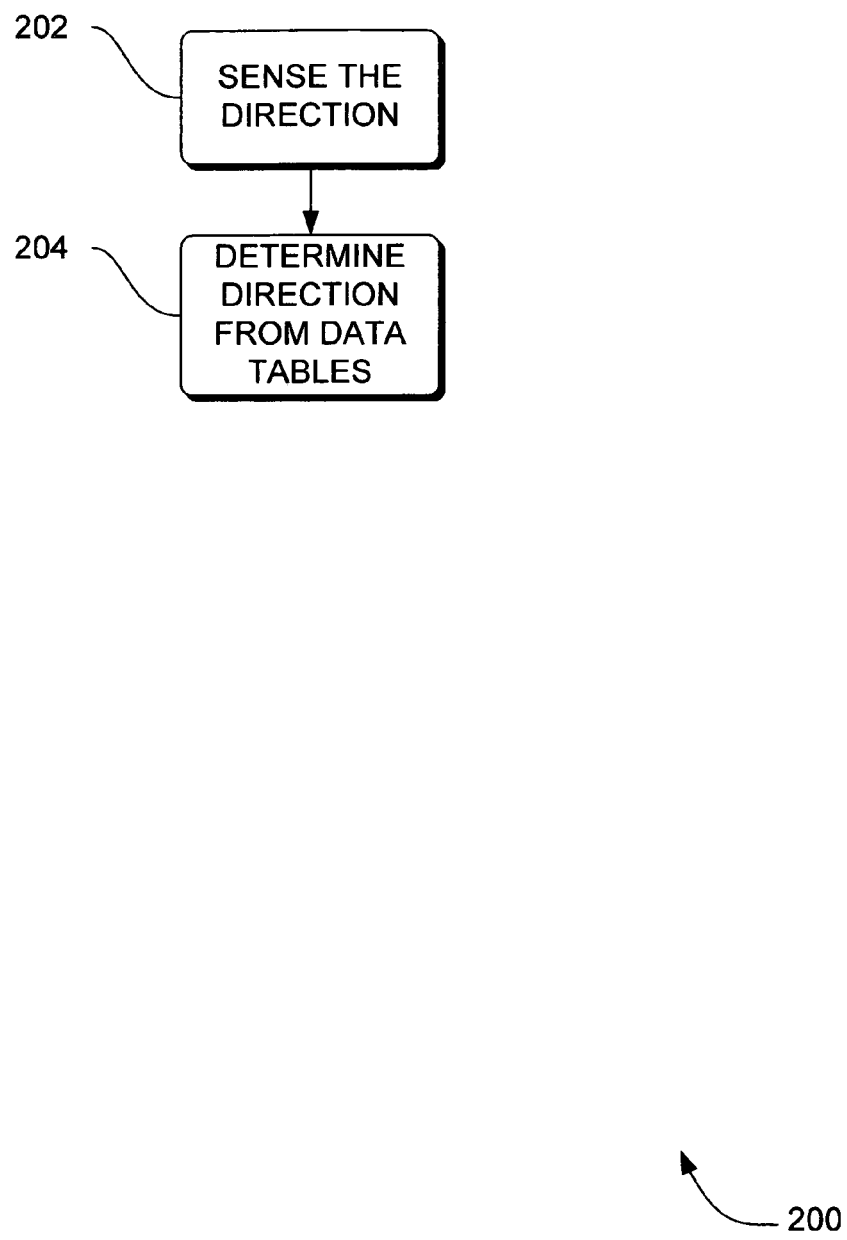
FIG. 2 is a flowchart of a method to determine a direction of a manually-propelled movement of the medical imaging positioning apparatus using a sensor and a data table according to an embodiment.

FIG. 2 is a flowchart of a method 200 to determine a direction of a manually-propelled movement of the medical imaging positioning apparatus using a sensor and a data table according to an embodiment. Method 200 solves the need in the art to more easily move the positioning apparatus. Method 200 is one embodiment of determining 102 a direction of a manually-propelled movement of the medical imaging positioning apparatus in method 200 above.

Method 200 includes sensing 202 the direction of the manually-propelled movement of the positioning apparatus.

In some embodiments, method 200 also includes determining 204 the kinetic assistance from a table of forces and positions.

Figure 3:
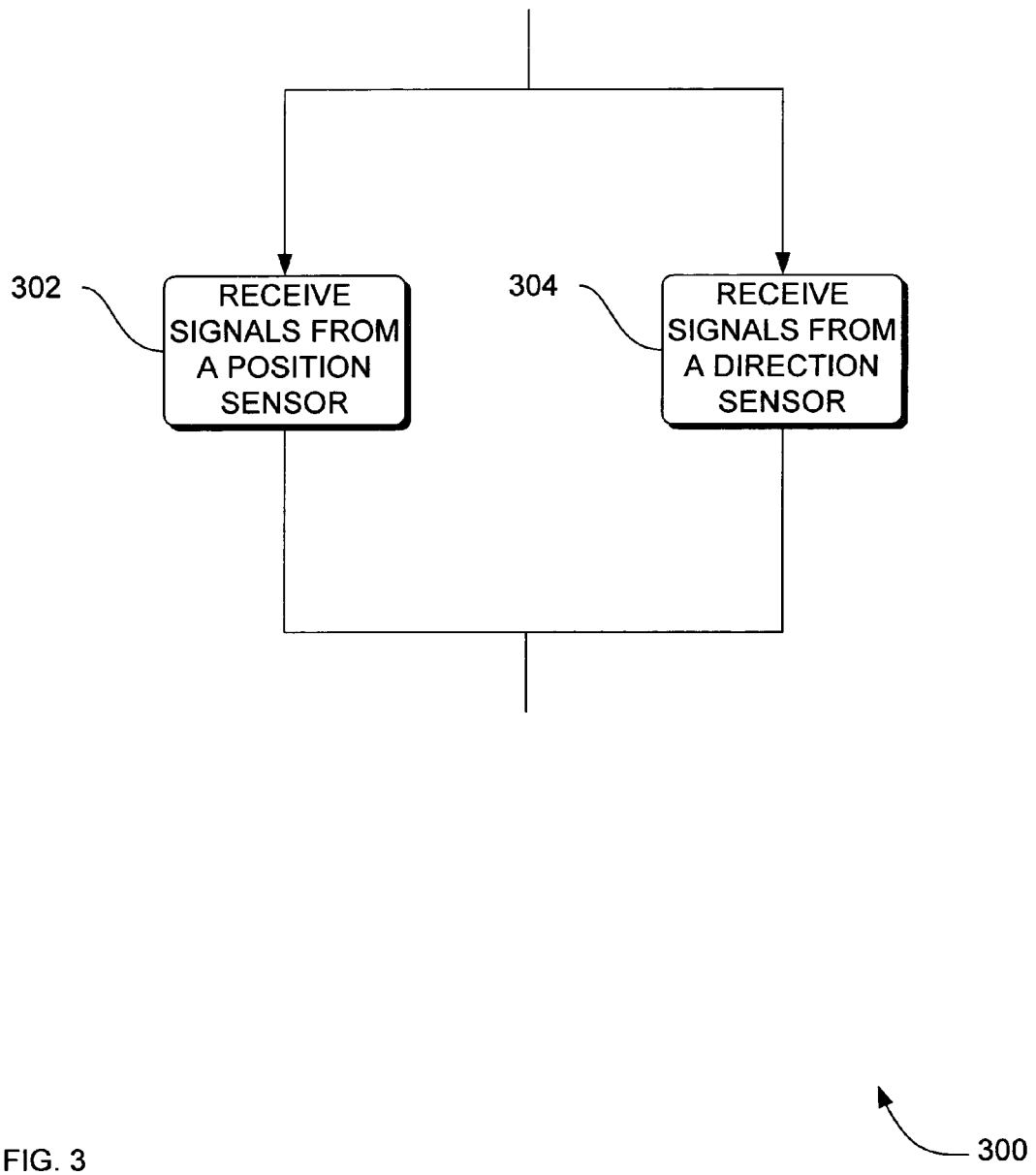
FIG. 3 is a flowchart of a method to determine a direction of a manually-propelled movement of the medical imaging positioning apparatus using a sensor according to an embodiment.

FIG. 3 is a flowchart of a method 300 to determine a direction of a manually-propelled movement of the medical imaging positioning apparatus using a sensor according to an embodiment. Method 300 is one embodiment of determining 102 a direction of a manually-propelled movement of the medical imaging positioning apparatus in method 200 above. Method 300 solves the need in the art to more easily move the positioning apparatus.

In some embodiments, method 300 includes receiving 302 a plurality of signals from a position sensing device. Examples of the sensing device include an encoder, a potentiometer and a resolver. The plurality of signals represent two or more measurements of a position of the medical imaging positioning apparatus performed on at least two different times.

In some embodiments, method 300 also includes receiving 304 a plurality of signals from a binary direction sensing device.

Figure 4:
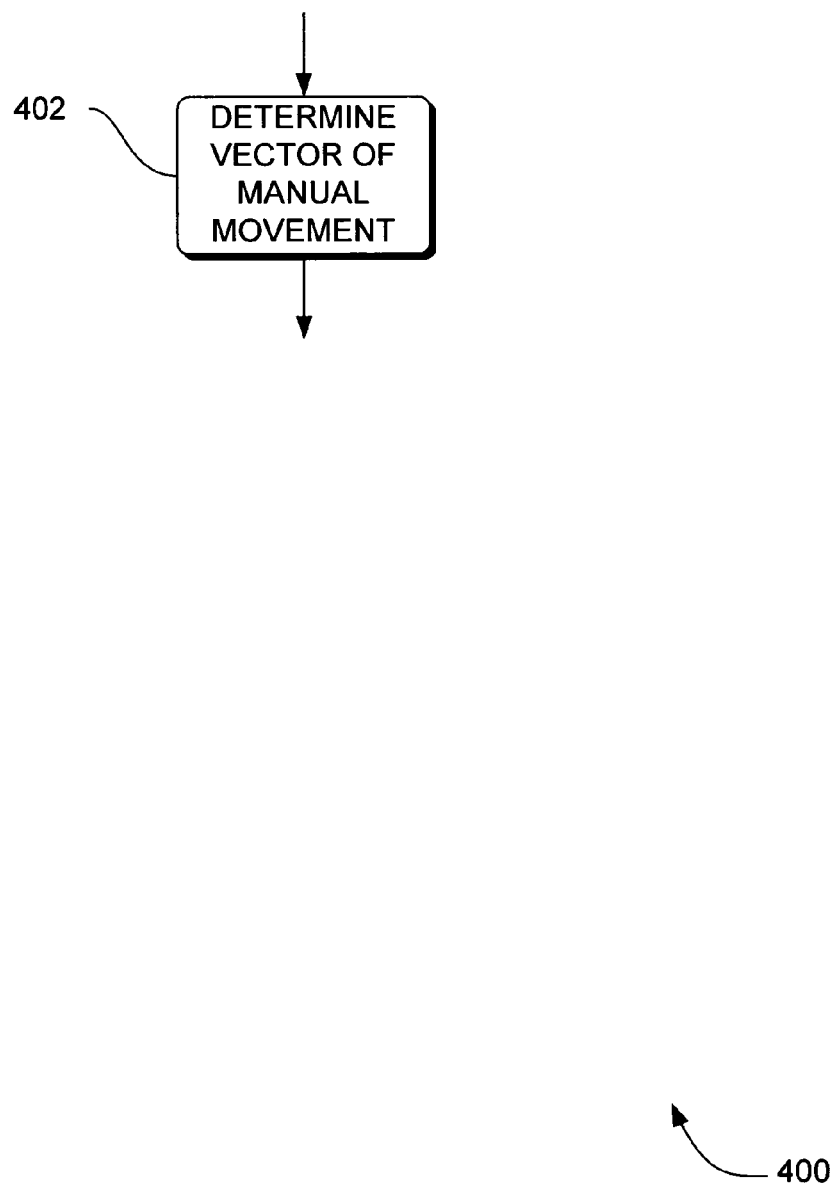
FIG. 4 is a flowchart of a method to determine a vector of a manually-propelled movement of the medical imaging positioning apparatus according to an embodiment.

FIG. 4 is a flowchart of a method 400 to determine a vector of a manually-propelled movement of the medical imaging positioning apparatus according to an embodiment. Method 400 solves the need in the art to more easily move the positioning apparatus. Method 400 is one embodiment of determining 102 a direction of a manually-propelled movement of the medical imaging positioning apparatus in method 200 above.

Method 400 includes determining 402 the vector of the manually-propelled movement of the medical imaging positioning apparatus. The vector includes both a direction and a magnitude or velocity.

In some embodiments, determining 402 the vector includes determining a magnitude of the direction of the manually-propelled movement of the positioning apparatus. In some embodiments, determining 402 the vector includes receiving at least one signal from a velocity sensing device.

Figure 5:
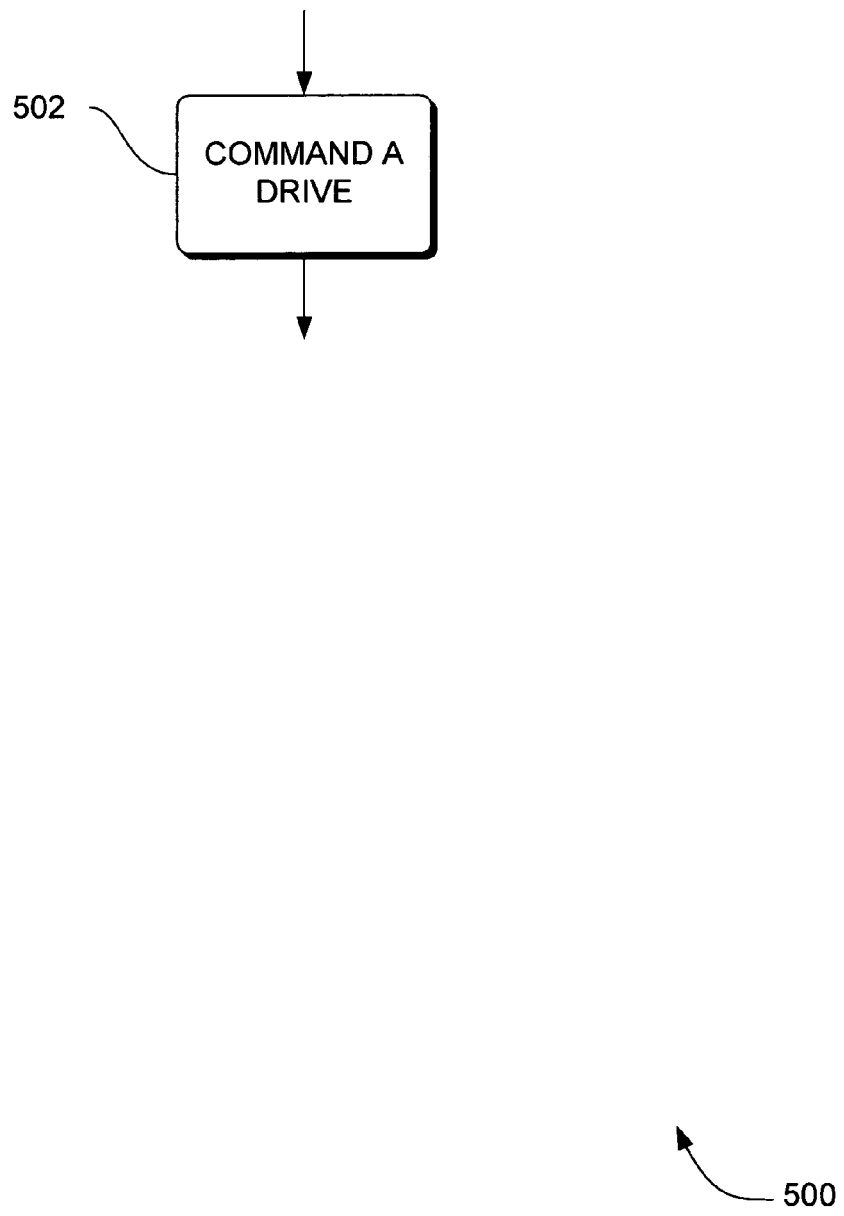
FIG. 5 is a flowchart of a method to apply a kinetic assistance to the medical imaging positioning equipment according to an embodiment.

FIG. 5 is a flowchart of a method 500 to apply a kinetic assistance to the medical imaging positioning equipment according to an embodiment. Method 500 is one embodiment of action 104 in FIG. 1 of applying a kinetic assistance to the medical imaging positioning equipment. Method 500 solves the need in the art to more easily move the positioning apparatus.

Method 500 includes commanding 502 distribution of a magnitude of electrical energy to a drive of the medical imaging positioning apparatus. In embodiments where the medical imaging positioning apparatus is moved in rotation and/or along three axes, distribution of electrical energy is commanded to at least one drive of the one or more of the axes.

Figure 6:
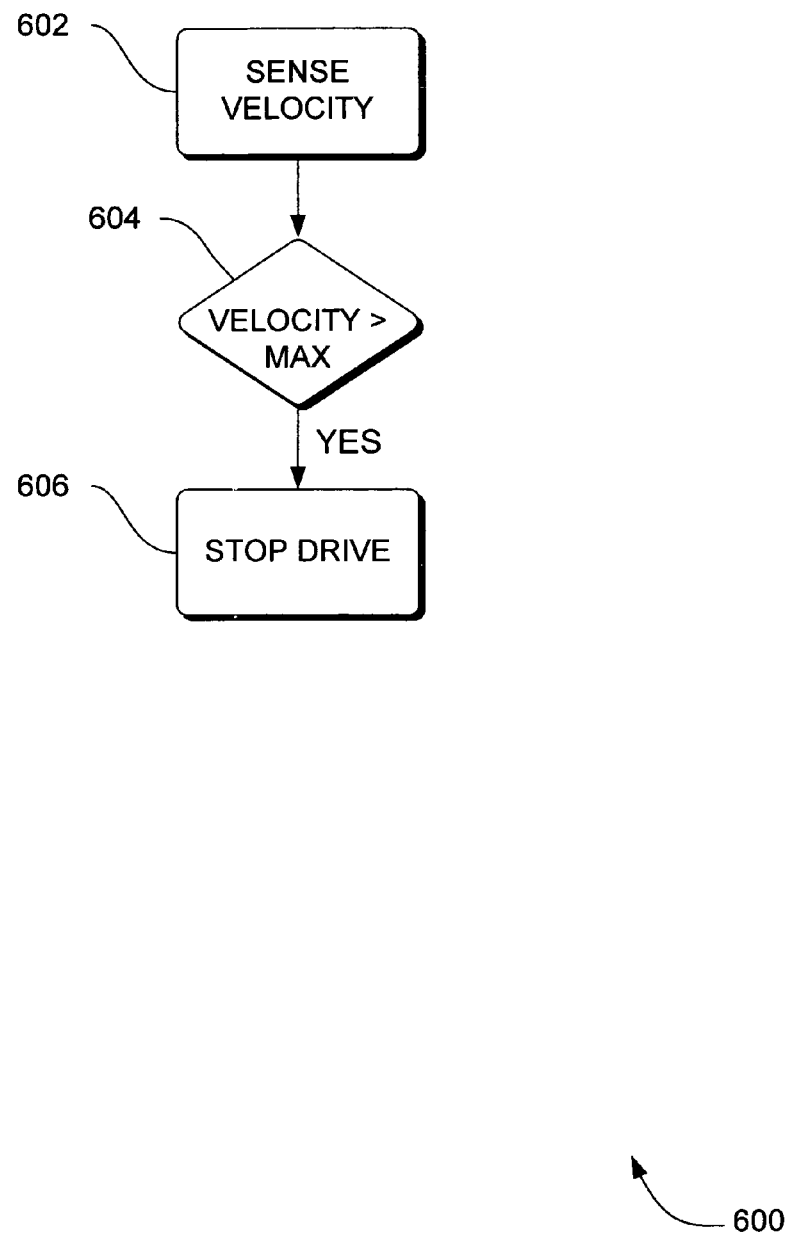
FIG. 6 is a flowchart of a method to apply a kinetic assistance to the medical imaging positioning equipment according to an embodiment.

FIG. 6 is a flowchart of a method 600 to apply a kinetic assistance to the medical imaging positioning equipment according to an embodiment. Method 600 is one embodiment of action 104 in FIG. 1 of applying a kinetic assistance to the medical imaging positioning. Method 600 solves the need in the art to more easily move the positioning apparatus.

Method 600 includes sensing 602 a velocity of the medical imaging positioning apparatus. Thereafter the velocity is tested to determine 604 if the velocity is greater than a maximum speed. If the speed is greater than the maximum speed, then the engaging means for the drive is disengaged, and the power supply to a drive of the medical imaging positioning apparatus is commanded 606 to cease or reduce supply of electrical power to the medical imaging positioning apparatus. Method 600 permits the operator to operate the equipment at any desired speed, while limiting the kinetic assistance to speeds below some maximum value which is determined by considerations including the maximum speed possible for the means of providing kinetic assistance, and the range of speeds for which providing kinetic assistance is considered prudent by the equipment manufacturer.

Figure 7:
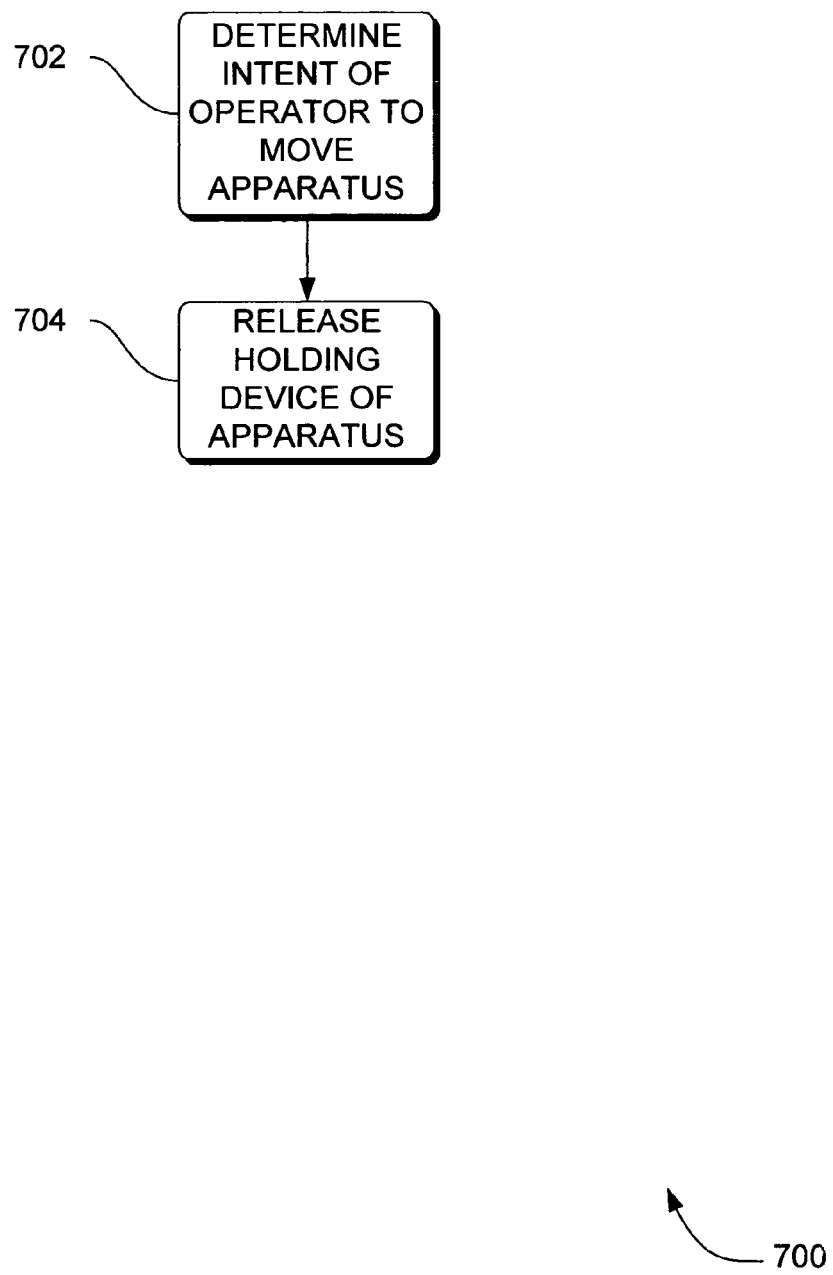
FIG. 7 is a flowchart of a method to operate a medical imaging positioning apparatus according to an embodiment.

FIG. 7 is a flowchart of a method 700 to operate a medical imaging positioning apparatus according to an embodiment. Method 700 solves the need in the art to more easily move the positioning apparatus.

Method 700 includes releasing 702 at least one holding device which maintains the medical imaging positioning apparatus in a start position. Thereafter, method 700 includes determining 704 an intention of an operator in movement of the medical imaging positioning equipment.

Figure 8:
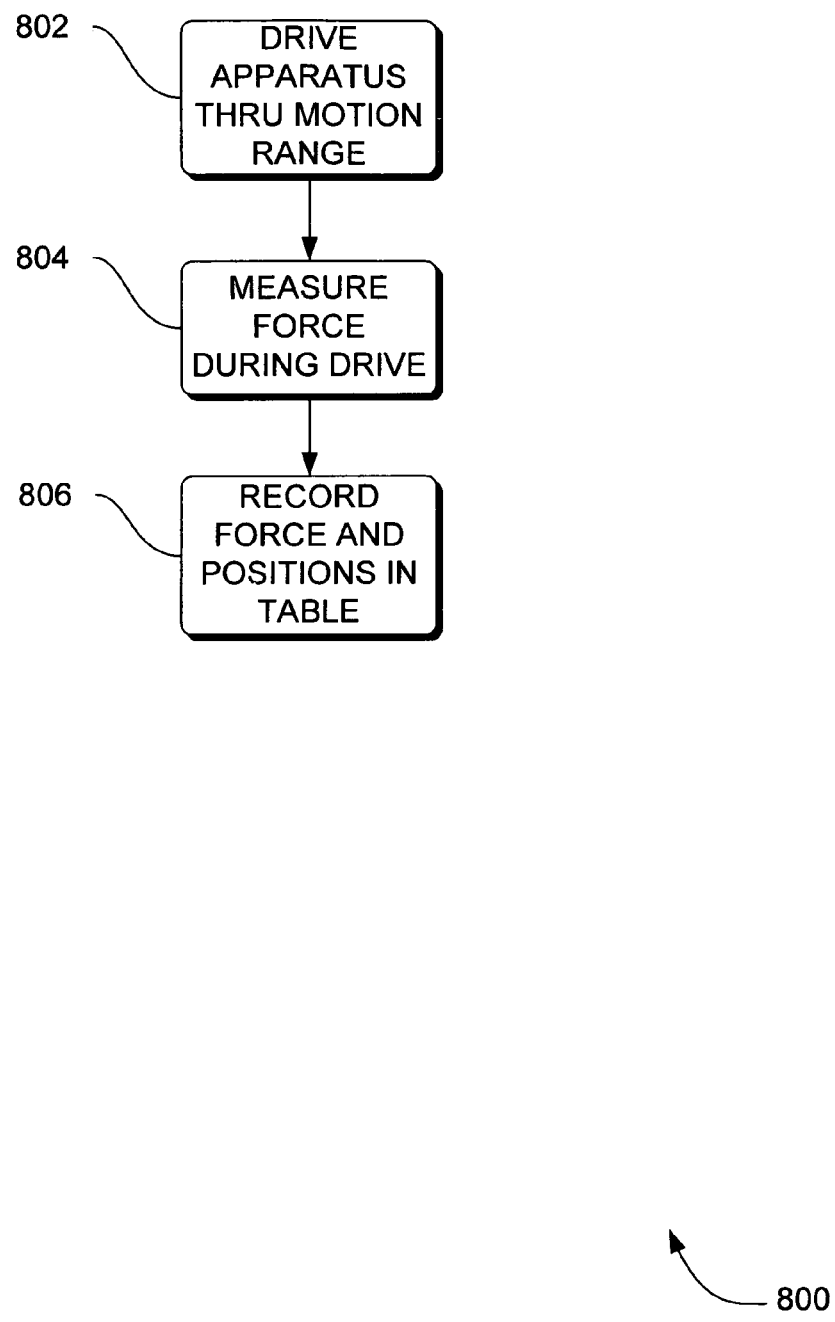
FIG. 8 is a flowchart of a method to generate a table of forces and positions in a movement of a medical imaging positioning apparatus according to an embodiment.

FIG. 8 is a flowchart of a method 800 to generate a table of forces and positions in a movement of a medical imaging positioning apparatus according to an embodiment.

Method 800 includes driving 802 the medical imaging positioning apparatus through a range of motion of the medical imaging positioning apparatus. The driving 802 is propulsion of the medical imaging positioning apparatus through any means, such as by a drive motor operably coupled to the medical imaging positioning apparatus.

Method 800 also includes measuring 804 the force at a plurality of points with the range of motion that is required to move the medical imaging positioning apparatus. Thereafter, the forces are recorded 804 in a table of forces and positions. More specific embodiments of the actions in FIG. 8 are described in method 900 below.

Figure 9:
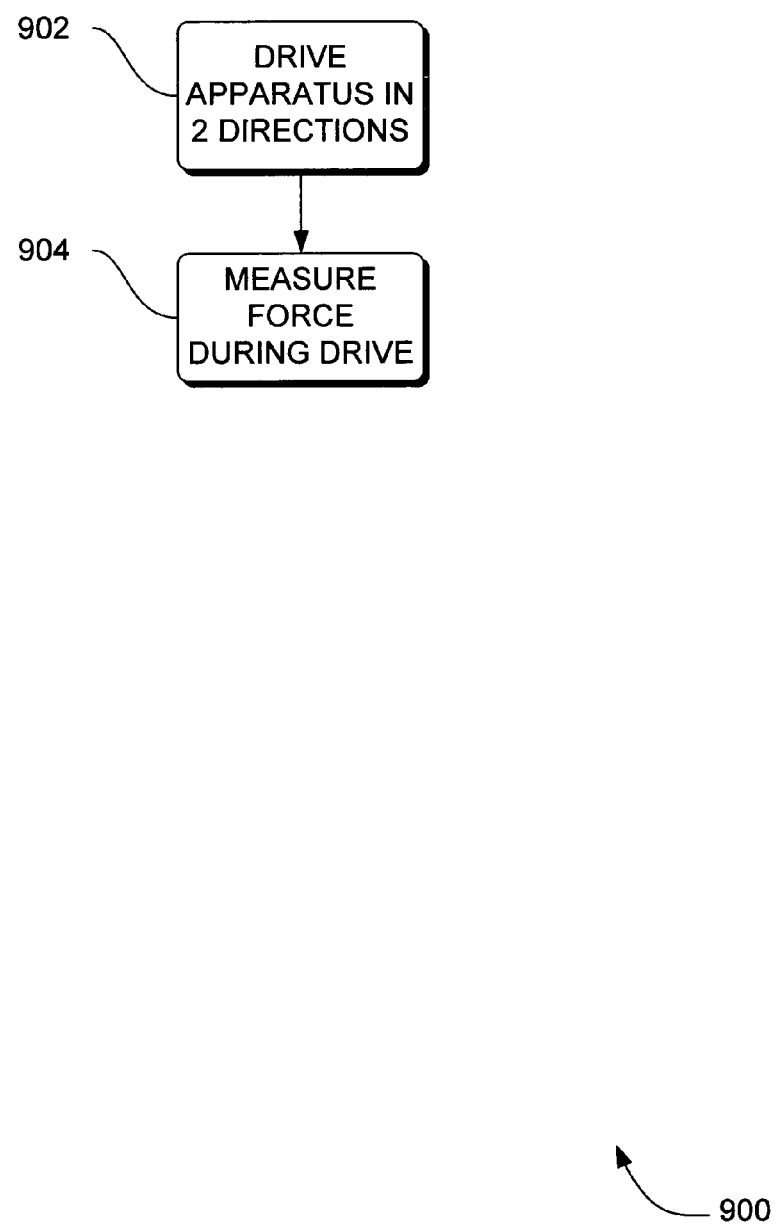
FIG. 9 is a flowchart of a method of specific steps to generate a table of forces and positions in a movement of a medical imaging positioning apparatus according to an embodiment.

FIG. 9 is a flowchart of a method 900 of specific steps to generate a table of forces and positions in a movement of a medical imaging positioning apparatus according to an embodiment.

Method 900 includes driving 902 the medical imaging positioning apparatus in two directions of motion. Driving 902 in two different directions is one embodiment of driving 802 through a range of motions in FIG. 8 above.

Method 900 also includes measuring 904 in the two directions of motion. Measuring 904 in two different directions is one embodiment of measuring 804 in the range of motion in FIG. 8 above.

Figure 13:
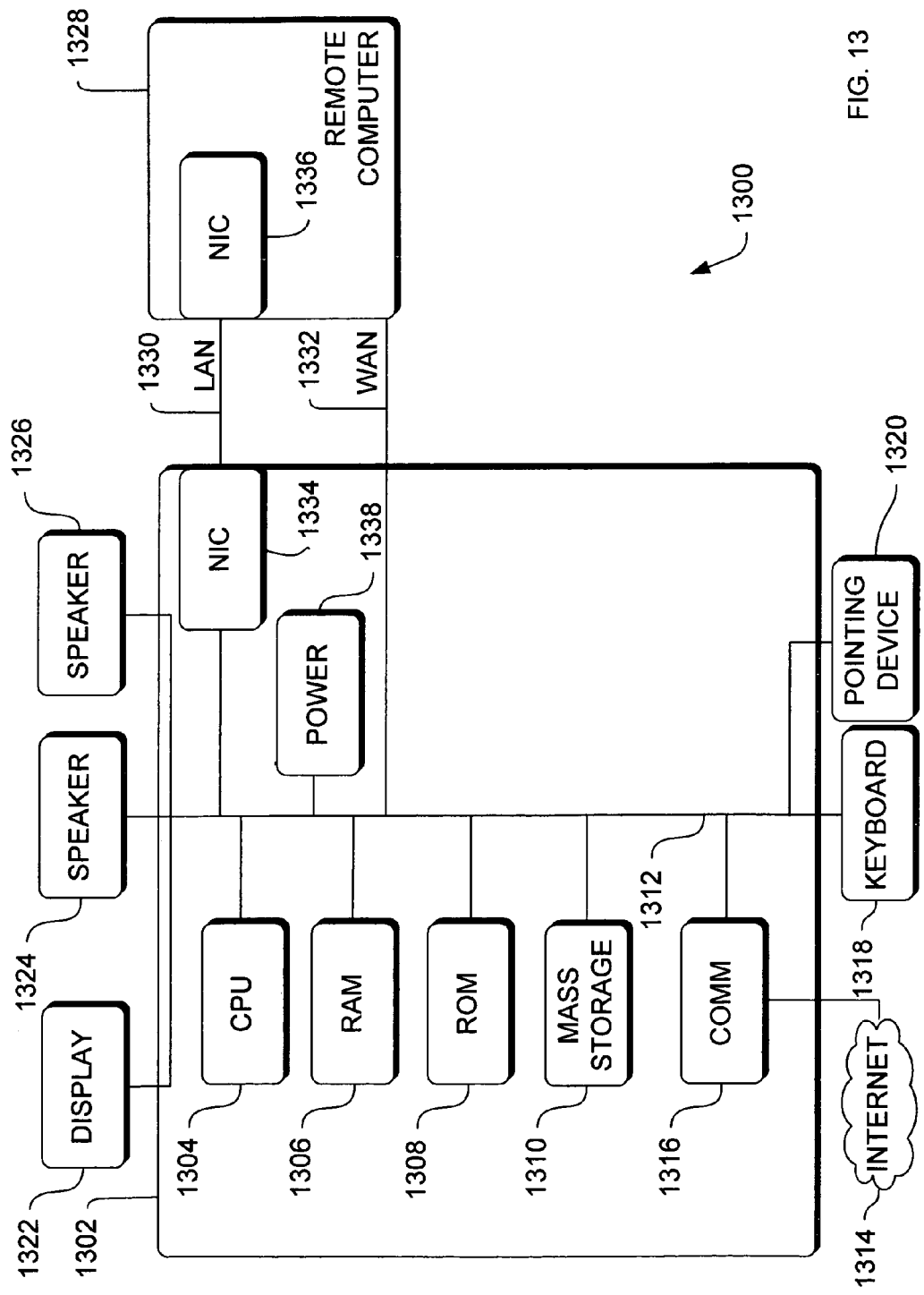
FIG. 13 is a block diagram of the hardware and operating environment in which different embodiments can be practiced.

In some embodiments, methods 100-900 are implemented as a computer data signal embodied in a carrier wave, that represents a sequence of instructions which, when executed by a processor, such as processor 1304 in FIG. 13, cause the processor to perform the respective method. In other embodiments, methods 100-900 are implemented as a computer-accessible medium having executable instructions capable of directing a processor, such as processor 1304 in FIG. 13, to perform the respective method. In varying embodiments, the medium is a magnetic medium, an electronic medium, or an optical medium.

Apparatus of Embodiments

In the previous section, embodiments of methods of operation were described. In this section, the particular apparatus of such an embodiment are described by reference to a series of diagrams.

Figure 10:
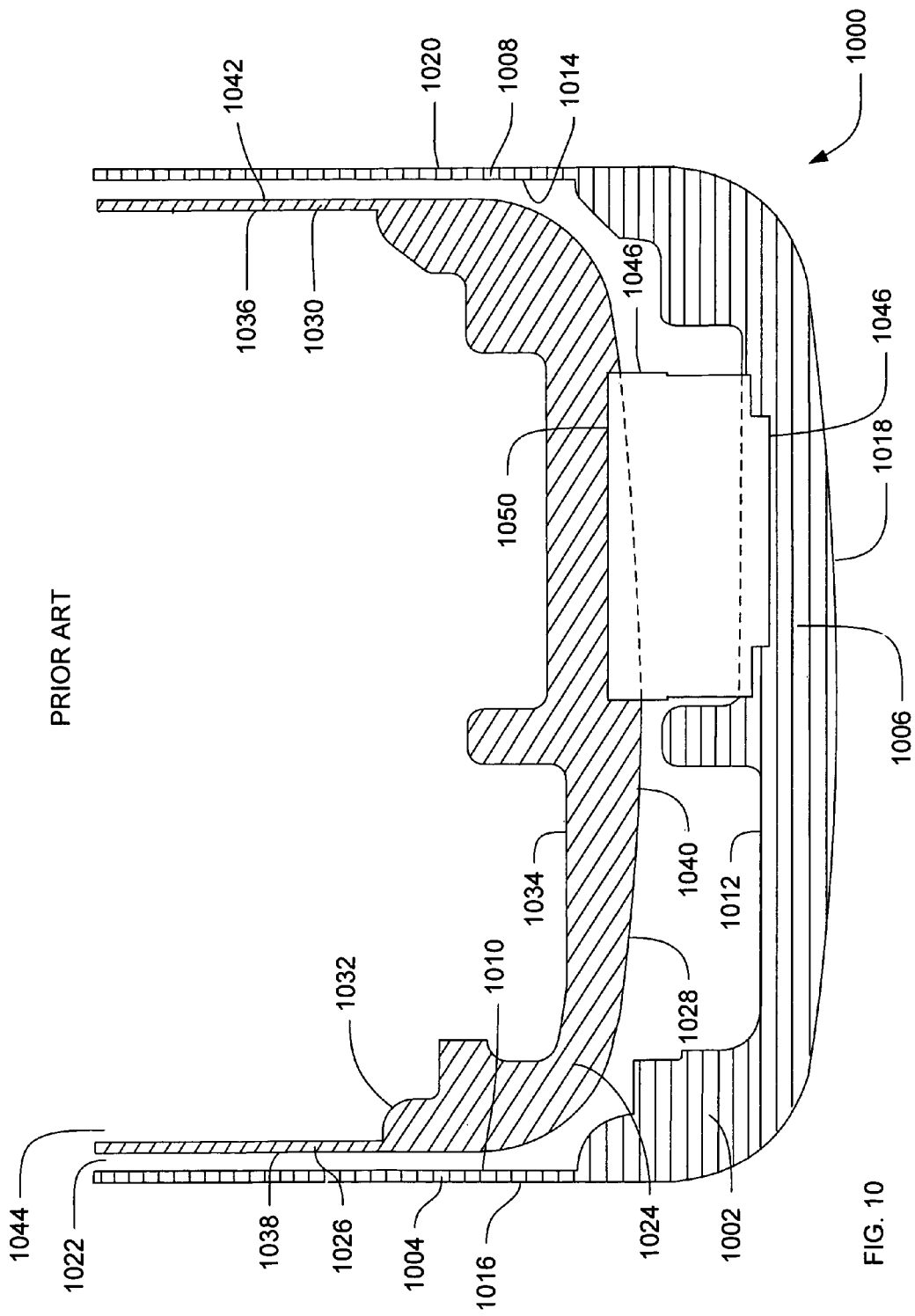
FIG. 10 is an end cross section diagram of medical imaging positioning apparatus according to an embodiment.

FIG. 10 is an end cross section diagram of medical imaging positioning apparatus 1000 according to an embodiment. Apparatus 1000 includes a first open section 1002. The first open section 1002 has three sides 1004, 1006 and 1008. Side 1006 is the middle side of first open section 1002 because side 1006 is located between sides 1004 and 1008. Sides 1004, 1006 and 1008 have inner faces 1010, 1012, 1014 and outer faces 1016, 1018 and 1020, respectively. The first open section also includes a side 1022 that is open. The open side 1022 lacks closure, thus providing a concave, "U" shape to the first open section 1002. The open side 1022 is opposite side 1006. The first open section 1002 also has two ends that are not shown in this cross section diagram 1000, each end having an inner face and an outer face. First open section 1002 and apparatus 1000 also have a longitudinal axis, which is also not shown in FIG. 10. In apparatus 1000, the first linear slide base 104 is implemented as a second open section 1024. The second open section 1024 is similar to the first open section 1002 in that the second open section 1024 is concave, but with one notable difference: The second open section 1024 is smaller than the first open section 1002 to the extent that second open section 1024 fits into the first open section 1002. More specifically, the second open section 1024 has outer dimensions that are smaller than the inner dimensions of the first open section 1002.

The second open section 1024 has three sides 1026, 1028 and 1030. Side 1028 is the middle side of second open section 1024 because side 1028 is located between sides 1026 and 1030. Sides 1026, 1028 and 1030 have inner faces 1032, 1034, 1036 and outer faces 1038, 1040 and 1042, respectively. The second open section also includes a side 1044 that is open. The open side 1044 lacks closure, thus providing a concave, "U" shape to the second open section 1024. The open side 1044 is opposite side 1028. The second open section 1024 also has two ends that are not shown in this cross section diagram 1000, each end having an inner face and an outer face. Second open section 1024 and apparatus 1000 also have a longitudinal axis, which is also not shown in FIG. 10. The longitudinal axis of the second open section 1024 is aligned in parallel with the longitudinal axis of the first open section 1002.

The apparatus 1000 also includes a first linear bearing assembly 1046. The first linear assembly 1046 has a first side 1048 and a second side 1050. Both sides 1048 and 1050 are parallel to a motion of the at least one first linear bearing assembly 1046. The first side 1048 of the first linear bearing assembly 1046 is mounted to the first open section 1002 on the inner face 1012 of the side 1006 that is opposite the open side 1022 of the first open section 1002. The second side 1050 of the first linear bearing assembly 1046 is mounted to the second open section 1024 on the outer face 1040 of the side 1028 of the second open section 1028 that is opposite the open side 1044 of the second open section 1024.

Figure 11:
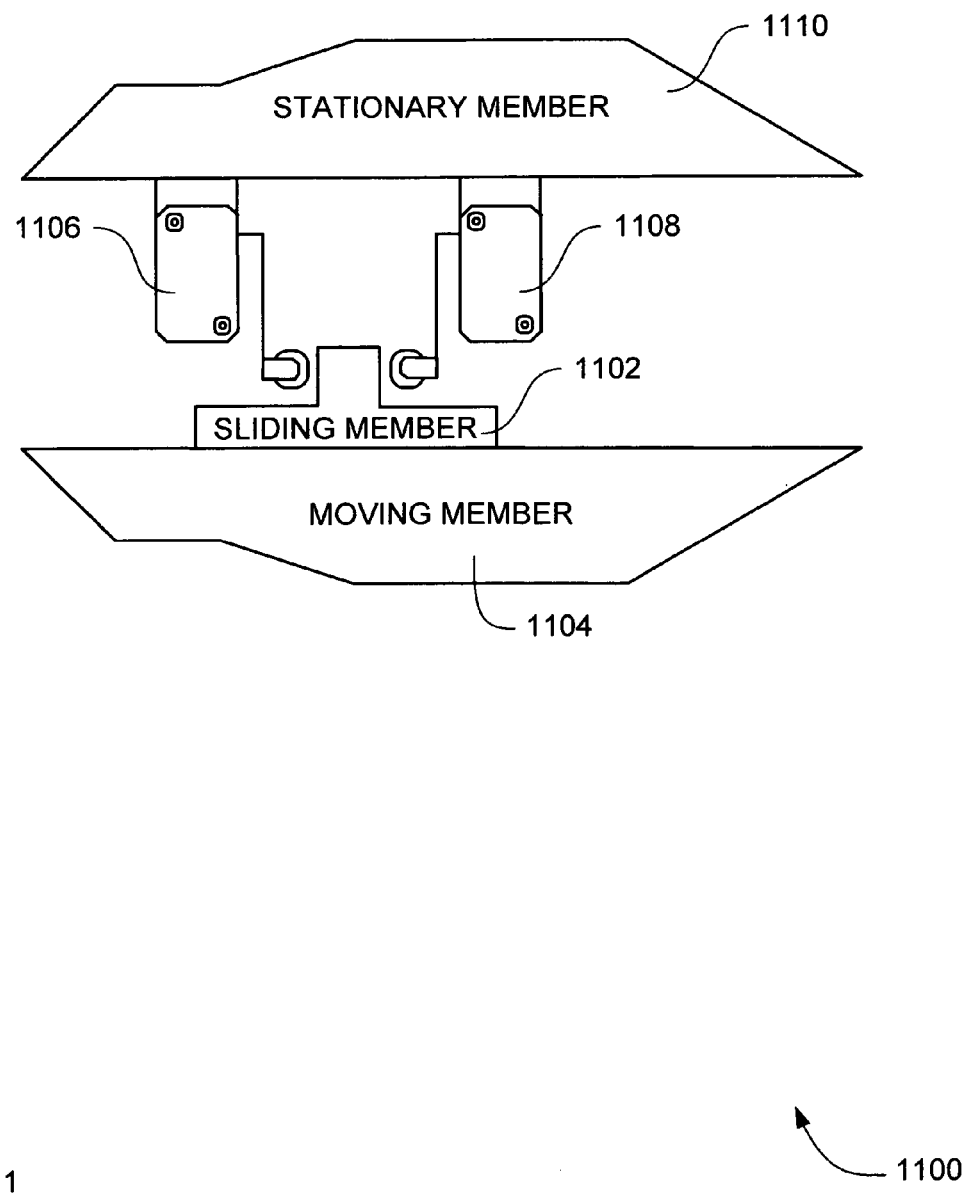
FIG. 11 is an end cross section diagram of medical imaging positioning apparatus according to an embodiment.

FIG. 11 is an end cross section diagram of medical imaging positioning apparatus 1100 according to an embodiment.

Apparatus 1000 includes a sliding member 1102 that is operably coupled to moving member 1104. One example of a moving member 1104 is the first open section 1002 in FIG. 10 above. The moving member 1104 is medical imaging equipment or some other item fixedly attached to the moving member 1104. The sliding member 1102 slides with friction along moving member 1104. The frictional force of moving member 1104 through sliding member 1102 actuates at least one direction sensing switch 1106 1108 disposed on a stationary member 1110. One example of a moving member 1104 is the second open section 1024 in FIG. 10 above. The stationary member 1110 is a support of the medical imaging equipment or an item fixedly coupled to the stationary member 1110.

In some embodiments, the direction sensing switches 1106 and 1108 are disposed on the moving member 1104 and the sliding member 1102 is operably coupled to the stationary member 1110. In some embodiments, the direction sensing switches 1106 and 1108 are replaced by other sensing apparatus, such as an optical interrupters and/or proximity probes. In some embodiments limit stops and guides are implemented to constrain motion of the sliding member. In some embodiments, apparatus are implemented to control the frictional force between the sliding member 1102 and the moving member 1104.

Figure 12:
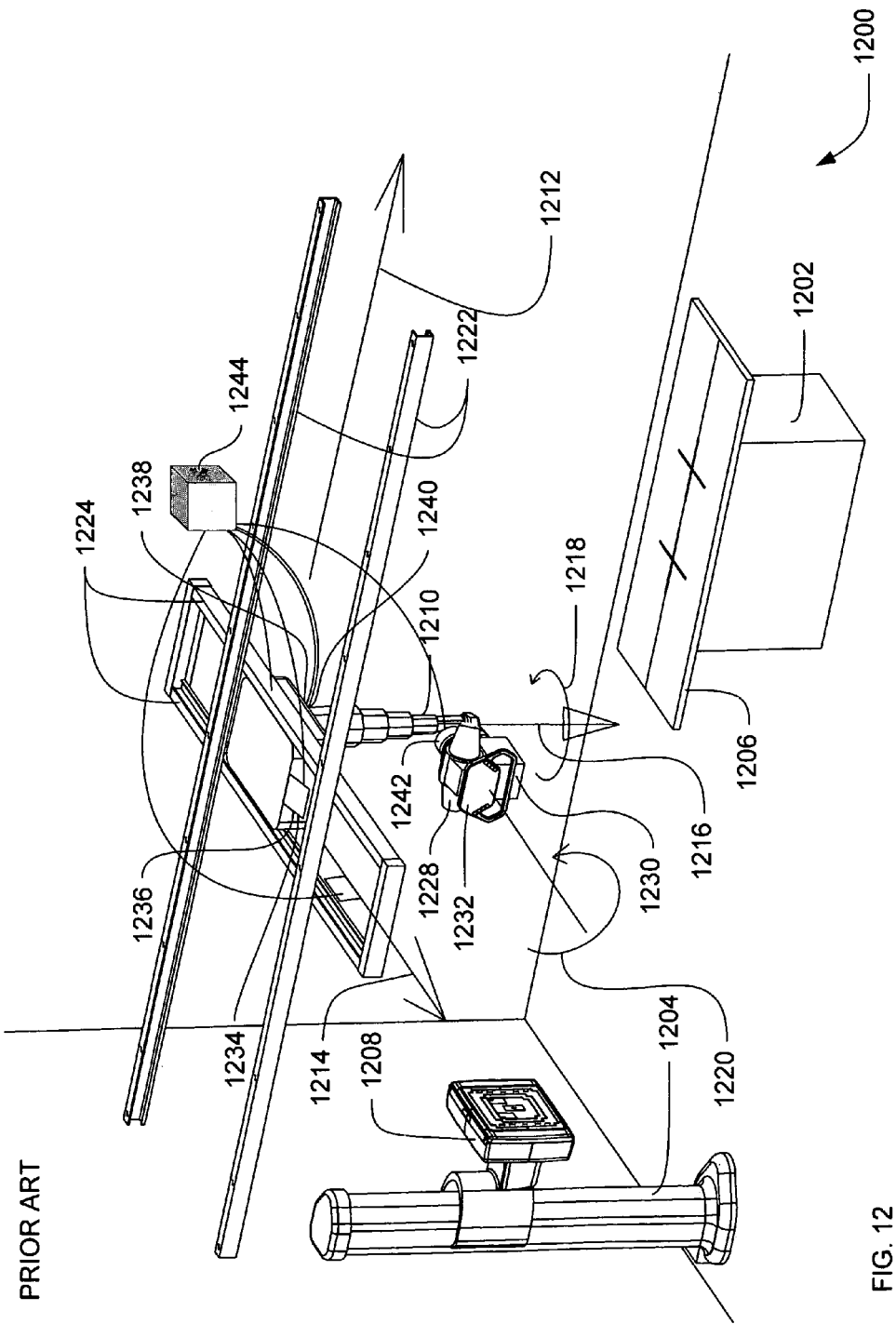
FIG. 12 is a block diagram that provides a system level overview of an asymmetrical extending column that includes linear bearings to provide freedom of motion for general positioning of imaging apparatus at a desired location and orientation.

FIG. 12 is a diagram of a radiographic positioning apparatus 1200. Apparatus 1200 includes a radiographic table 1202 and/or a radiographic wallstand 1204. The radiographic table 1202 and the wallstand 1204 each contain an image receptor, 1206 and 1208, respectively.

An overhead tube support (OTS) 1210 for performing diagnostic imaging procedures is also included. The OTS 1210 provides three linear motions (longitudinal X 1212, lateral Y 1214 and vertical Z 1216) which are perpendicular to each other, and two rotational rotations (rotation about the vertical axis "a" 1218, and rotation about one horizontal axis "b" 1220).

Longitudinal positioning rails 1222 are mounted to a ceiling (not shown). Lateral positioning rails 1224 move along the longitudinal positioning rails 1222 in the longitudinal X 1212 motion. In other embodiments, the lateral positioning rails 1224 are mounted to a ceiling and the longitudinal positioning rails 1222 move along the lateral positioning rails 1224 in the lateral Y 1214 motion.

A carriage 1226 moves along lateral positioning rails 1224 in the lateral Y 1214 motion. The OTS 1210 is mounted on the carriage 1226. A tube mount assembly 1232 includes an X-ray source 1228 and collimator 1230. The tube mount assembly 1232 is mounted to the OTS 1210. The tube mount assembly 1232 and/or the OTS 1210 rotate about the vertical "a" 1218 axis and the vertical "b" 1220 axis.

The OTS 1210 can be positioned at any attitude and position within the reaches of radiographic apparatus 1200. This flexibility in positioning is important in achieving alignment of the OTS 1210 to an image receptor for imaging of a subject that is positioned on the radiographic table 1202 or the radiographic wallstand 1204. The alignment of the OTS 1210 with an image receptor may be directed and/or controlled automatically by a control unit 1244 or the alignment may be directed and/or controlled manually.

The lateral positioning rails 1224 are operably coupled to the longitudinal positioning rails 1222 through one or more first motorized drives 1234. The carriage 1226 is operably coupled to the lateral positioning rails 1224 through one or more second motorized drives 1236. In some embodiments, the OTS 1210 is operably coupled to the carriage 1226 through one or more third motorized drives 1238 that rotates the OTS about the vertical Z 1216. In some embodiments, the OTS 1210 is also operably coupled to the carriage 1226 through one or more fourth motorized drives 1240 that extends the OTS along the vertical Z 1216. In some embodiments, the X-ray source 1228 is operably coupled to the OTS 1210 through one or more fifth motorized drives 1242 that rotate the X-ray source 1228 about the horizontal axis "b" 1220.

Each motorized drive includes a motor, and a position feedback measuring device, and in some embodiments a clutch and/or a lock or a brake. Each position feedback measuring device further includes a potentiometer, an encoder, a resolver, or a similar device. In the embodiments that lack a clutch, an efficient motor (having high quality bearings and high quality gears) is directly coupled, so that in manual motion the operator causes rotation of the motor armature as well as the OTS.

A control unit 1244 is operably coupled to the one or more first motorized drives 1234, the one or more second motorized drives 1236, the one or more third motorized drives 1238, the one or more fourth motorized drives 1240 and the one or more fifth motorized drives 1242. The control unit 1244 controls operation of the motorized drives, which positions the X-ray source 1228 and collimator 1230 into alignment with a radiographic receptor 1206 or 1208.

In some implementations, more than one control unit 1244 is included in apparatus 1200. Each control unit controls one or more motorized drives 1234, 1236, 1238, 1240 and/or 1242. For example, in one implementation apparatus 1200 includes one control unit for each motorized drive. Each control unit communicates with the other control units, directly, or through other computers. Each control unit includes a processor, such as processor 1304 in FIG. 13.

In apparatus 1200, a control unit 1244 controls the motorized drives to position the X-ray source 1228 and collimator 1230 into alignment with a radiographic receptor 1206 or 1208.

Hardware and Operating Environment

FIG. 13 is a block diagram of the hardware and operating environment 1300 in which different embodiments can be practiced. The description of FIG. 13 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment. Some embodiments can be implemented using commands stored in a Floating Point Gate Array, or similar hardware/firmware devices, and additionally, some embodiments can be implemented using hardware and analog components only Computer 1302 includes a processor 1304, commercially available from Intel, Motorola, Cyrix and others. Computer 1302 also includes random-access memory (RAM) 1306, read-only memory (ROM) 1308, and one or more mass storage devices 1310, and a system bus 1312, that operatively couples various system components to the processing unit 1304. The memory 1306, 1308, and mass storage devices, 1310, are types of computer-accessible media. Mass storage devices 1310 are more specifically types of nonvolatile computer-accessible media and can include one or more hard disk drives, floppy disk drives, optical disk drives, and tape cartridge drives. The processor 1304 executes computer programs stored on the computer-accessible media.

Computer 1302 can be communicatively connected to the Internet 1314 via a communication device 1316. Internet 1314 connectivity is well known within the art. In one embodiment, a communication device 1316 is a modem that responds to communication drivers to connect to the Internet via what is known in the art as a "dial-up connection." In another embodiment, a communication device 1316 is an Ethernet® or similar hardware network card connected to a local-area network (LAN) that itself is connected to the Internet via what is known in the art as a "direct connection" (e.g., T1 line, etc.).

A user enters commands and information into the computer 1302 through input devices such as a keyboard 1318 or a pointing device 1320. The keyboard 1318 permits entry of textual information into computer 1302, as known within the art, and embodiments are not limited to any particular type of keyboard. Pointing device 1320 permits the control of the screen pointer provided by a graphical user interface (GUI) of operating systems such as versions of Microsoft Windows®. Embodiments are not limited to any particular pointing device 1320. Such pointing devices include mice, touch pads, trackballs, remote controls and point sticks. Other input devices (not shown) can include a microphone, joystick, game pad, satellite dish, scanner, or the like.

In some embodiments, computer 1302 is operatively coupled to a display device 1322. Display device 1322 is connected to the system bus 1312. Display device 1322 permits the display of information, including computer, video and other information, for viewing by a user of the computer. Embodiments are not limited to any particular display device 1322. Such display devices include cathode ray tube (CRT) displays (monitors), as well as flat panel displays such as liquid crystal displays (LCD's). In addition to a monitor, computers typically include other peripheral input/output devices such as printers (not shown). Speakers 1324 and 1326 provide audio output of signals. Speakers 1324 and 1326 are also connected to the system bus 1312.

Computer 1302 also includes an operating system (not shown) that is stored on the computer-accessible media RAM 1306, ROM 1308, and mass storage device 1310, and is and executed by the processor 1304. Examples of operating systems include Microsoft Windows®, Apple MacOS®, Linux®, UNIX®. Examples are not limited to any particular operating system, however, and the construction and use of such operating systems are well known within the art.

Embodiments of computer 1302 are not limited to any type of computer 1302. In varying embodiments, computer 1302 comprises a PC-compatible computer, a MacOS®-compatible computer, a Linux®-compatible computer, or a UNIX®-compatible computer. The construction and operation of such computers are well known within the art.

Computer 1302 can be operated using at least one operating system to provide a graphical user interface (GUI) including a user-controllable pointer. Computer 1302 can have at least one web browser application program executing within at least one operating system, to permit users of computer 1302 to access intranet or Internet world-* wide-web pages as addressed by Universal Resource Locator (URL) addresses. Examples of browser application programs include Netscape Navigator® and Microsoft Internet Explorer®.

The computer 1302 can operate in a networked environment using logical connections to one or more remote computers, such as remote computer 1328. These logical connections are achieved by a communication device coupled to, or a part of, the computer 1302. Embodiments are not limited to a particular type of communications device. The remote computer 1328 can be another computer, a server, a router, a network PC, a client, a peer device or other common network node. The logical connections depicted in FIG. 13 include a local-area network (LAN) 1330 and a wide-area network (WAN) 1332. Such networking environments are commonplace in offices, enterprise-wide computer networks, intranets and the Internet.

When used in a LAN-networking environment, the computer 1302 and remote computer 1328 are connected to the local network 1330 through network interfaces or adapters 1334, which is one type of communications device 1316. Remote computer 1328 also includes a network device 1336. When used in a conventional WAN-networking environment, the computer 1302 and remote computer 1328 communicate with a WAN 1332 through modems (not shown). The modem, which can be internal or external, is connected to the system bus 1312. In a networked environment, program modules depicted relative to the computer 1302, or portions thereof, can be stored in the remote computer 1328.

Computer 1302 also includes power supply 1338. Each power supply can be a battery.

CONCLUSION

A positioning apparatus movement assistance system is described. Although specific embodiments are illustrated and described herein, it will be appreciated by those of ordinary skill in the art that any arrangement which is calculated to achieve the same purpose may be substituted for the specific embodiments shown. This application is intended to cover any adaptations or variations.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future positioning apparatus and new medical imaging devices.

The terminology used in this application is meant to include all environments and alternate technologies which provide the same functionality as described herein.

I claim:

1. A computer-accessible medium having executable instructions to provide a kinetic assistance in a movement of a medical imaging positioning apparatus, the executable instructions capable of directing a processor to perform:
   determining at least one kinetic assistance of a manually-propelled movement of the medical imaging positioning apparatus;
   determining at least one direction from a table of forces and positions; and
   applying a kinetic assistance to the medical imaging positioning apparatus in the at least one direction.

2. The computer-accessible medium of claim 1, wherein the at least one direction further comprises:
   three axes; and
   a rotation.

3. The computer-accessible medium of claim 1, wherein the executable instructions capable of directing a processor to perform the determining further comprise executable instructions capable of directing a processor to perform:

sensing the at least one direction of the manually-propelled movement of the positioning apparatus.

4. The computer-accessible medium of claim 1, wherein the instructions further comprise instructions capable of directing a medical imaging positioning apparatus having:
an x-ray source.

5. The computer-accessible medium of claim 1, wherein the executable instructions capable of directing a processor to perform the determining further comprise executable instructions capable of directing a processor to perform:
receiving a plurality of signals from a position sensing device selected from the group consisting of an encoder, a potentiometer, and a resolver; the plurality of signals representing at least two measurements of a position of the medical imaging positioning apparatus performed on at least two different times.

6. The computer-accessible medium of claim 1, wherein the executable instructions capable of directing the processor to perform the determining further comprise executable instructions capable of directing the processor to perform:
receiving a plurality of signals from a binary direction sensing device.

7. The computer-accessible medium of claim 6, wherein the instructions further comprise instructions directing the processor to receive the plurality of signals from a binary direction sensing device having:
at least one switch.

8. The computer-accessible medium of claim 1, wherein the executable instructions capable of directing the processor to perform the determining further comprise executable instructions capable of directing the processor to perform:
determining a magnitude of the at least one direction of the manually-propelled movement of the positioning apparatus, wherein the at least one direction and the magnitude comprise a vector.

9. The computer-accessible medium of claim 8, wherein the executable instructions capable of directing the processor to perform determining the magnitude further comprise executable instructions capable of directing the processor to perform:
receiving at least one signal from a velocity sensing device.

10. The computer-accessible medium of claim 9, wherein the instructions further comprise instructions directing the processor to receive the at least one signal from a velocity sensing device having:
a tachometer.

11. The computer-accessible medium of claim 1, wherein the executable instructions capable of directing the processor to perform the applying further comprise executable instructions capable of directing the processor to perform:
commanding distribution of a magnitude of electrical energy to a drive of the medical imaging positioning apparatus.

12. The computer-accessible medium of claim 1, wherein the executable instructions capable of directing the processor to perform the applying further comprise executable instructions capable of directing the processor to perform:
sensing a velocity of the medical imaging positioning apparatus;
determining that the velocity is greater than a maximum speed; and
engaging apparatus for a drive is disengaged.

13. The computer-accessible medium of claim 1, wherein the kinetic assistance further comprises:
a kinetic assistance that varies in accordance to the at least one direction.

14. The computer-accessible medium of claim 1, the computer-accessible medium further comprises executable instructions capable of directing a processor to perform:
determining an intention of an operator in movement of the medical imaging positioning apparatus; and
releasing at least one holding device which maintains the medical imaging positioning apparatus in a start position.

15. A method of moving a medical imaging device that is operably coupled to a tube mount assembly, the method comprising:
releasing at least one holding device which maintains the tube mount assembly in a position;
sensing a vector of manually-propelled movement of the tube mount assembly, the vector including a magnitude;
determining a direction from a table of forces and positions; and applying a kinetic assistance to the tube mount assembly in the direction.

16. The method of claim 15, wherein the sensing further comprises:
receiving a plurality of signals from at least one position sensing device selected from the group consisting of an encoder, a potentiometer, and a resolver; the plurality of signals representing at least two measurements of a position of the tube mount assembly performed on at least two different times.

17. The method of claim 15, wherein the sensing further comprises: receiving at least one signal from a binary direction sensing device.

18. The method of claim 15, wherein the sensing further comprises: determining an intention of an operator in movement of the medical imaging tube mount assembly.

19. The method of claim 15, wherein the medical imaging device further comprises: using an X-ray source.

20. The method of claim 15, wherein applying a kinetic assistance to the tube mount assembly further comprises:
sensing a velocity of the tube mount assembly;
determining that the velocity is greater than a maximum speed; and disengaging a drive.

* * * * *